United States Patent
Podrebarac et al.

(10) Patent No.: US 7,220,886 B2
(45) Date of Patent: May 22, 2007

(54) OLEFIN METATHESIS

(75) Inventors: Gary G. Podrebarac, Houston, TX (US); John R. Adams, Houston, TX (US); Arvids Judzis, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 50 days.

(21) Appl. No.: 10/974,516

(22) Filed: Oct. 27, 2004

(65) Prior Publication Data

US 2006/0089517 A1    Apr. 27, 2006

(51) Int. Cl.
*G07C 1/00* (2006.01)
*G07C 6/00* (2006.01)

(52) U.S. Cl. .................. 585/646; 585/643; 585/644; 585/324

(58) Field of Classification Search .............. 585/643, 585/645–647, 324, 644
See application file for complete search history.

(56) References Cited

U.S. PATENT DOCUMENTS

| | | | |
|---|---|---|---|
| 3,261,879 A | 7/1966 | Banks | 260/683 |
| 3,365,513 A | 1/1968 | Heckelsberg | 260/683 |
| 3,697,613 A | 10/1972 | Arganbright | 260/683 D |
| 3,702,827 A | 11/1972 | Arganbright | 252/441 |
| 3,792,108 A | 2/1974 | Arganbright | 260/683 D |
| 3,923,920 A | 12/1975 | Regier | 260/683 D |
| 4,046,832 A | 9/1977 | Nowak et al. | 260/683 D |
| 4,709,115 A | 11/1987 | Jung et al. | 585/643 |
| 4,795,734 A | 1/1989 | Chauvin et al. | 502/355 |
| 5,026,936 A | 6/1991 | Leyshon et al. | 585/315 |
| 5,030,784 A | 7/1991 | Slaugh | 585/323 |
| 5,235,102 A | 8/1993 | Palmer et al. | 562/607 |
| 5,449,852 A | 9/1995 | Chauvin et al. | 585/647 |
| 5,596,115 A | 1/1997 | Commereuc | 556/27 |
| 6,420,619 B1 * | 7/2002 | Gartside et al. | 585/324 |
| 6,440,299 B2 * | 8/2002 | Hearn et al. | 208/189 |
| 6,583,329 B1 | 6/2003 | Podrebarac | 585/646 |

FOREIGN PATENT DOCUMENTS

EP    0 304 515 A1    3/1989
EP    0 664 776 B1    8/1995

* cited by examiner

*Primary Examiner*—Glenn Caldarola
*Assistant Examiner*—In Suk Bullock
(74) *Attorney, Agent, or Firm*—Kenneth H. Johnson

(57) ABSTRACT

A process for the production of propylene from the metathesis of ethylene and 2-butene is disclosed wherein a mixed $C_4$ stream is first treated to enrich and separate the 2-butene from 1-butene and isobutene by isomerization of 1-butene and concurrent fractional distillation of the 2-butene and isobutene to provide the 2-butene feed the metathesis with ethylene. In addition the mixed $C_4$ stream may be treated to remove mercaptans and dienes prior to 2-butene enrichment.

1 Claim, 1 Drawing Sheet

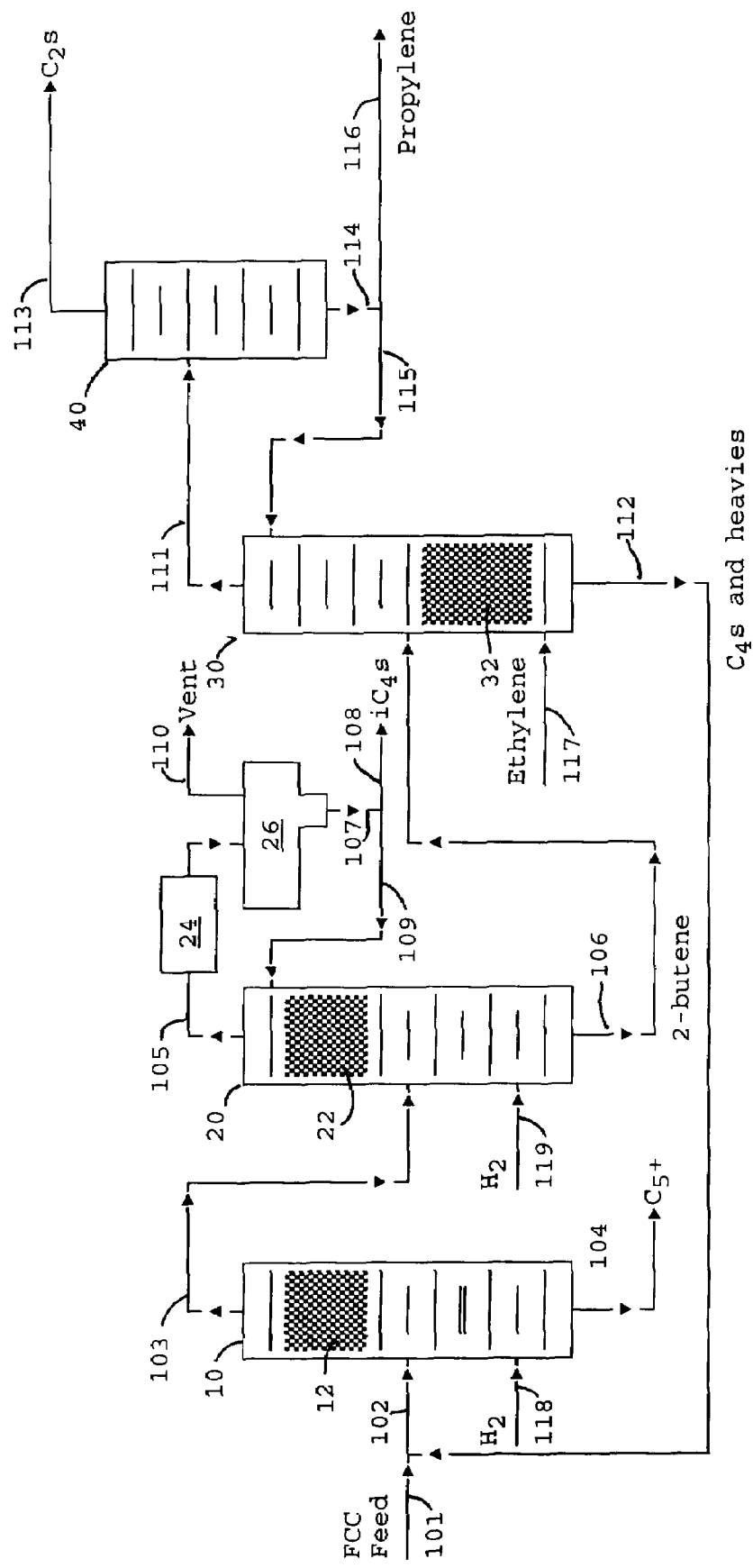

OLEFIN METATHESIS

BACKGROUND OF THE INVENTION

1. Field of the Invention

The present invention relates to a process for the metathesis of olefins. More particularly the invention relates to a process including the preparation of purified metathesis feed. More particularly the invention relates to a process wherein the catalyst is part of a distillation structure and the products are simultaneously separated from the reactants and each other by fractional distillation during the reaction.

2. Related Art

Broadly metathesis has been defined as a chemical reaction in which an element or radical in one compound changes places with another element or radical in another compound. See *The Van Nostrand Chemist's Dictionary*, D. Van Nostrand Company, Inc., 1953, page 463. More specifically olefin metathesis can be defined as the redistribution of alkylidene moieties to give a mixture of olefins. In effect, this reaction takes place via cleavage of the olefin double bond. Generally the reactions of olefinic molecules in the presence of metal-containing catalysts to produce other olefinic molecules are known in the art as "disproportionation", "dismutation" or "metathesis" reactions.

The metathesis reactions generally are of considerable interest because of the versatility of the reaction and the numerous olefinic hydrocarbons available from petrochemical sources which are suitable for use in the reaction to yield useful products. See, for example, U.S. Pat. No. 4,046,832 (metathesis of propylene with itself to produce n-butene and ethylene); U.S. Pat. No. 3,702,827 (the metathesis of 2-methyl-1-propene and 2-butene to produce 2-methyl-2-butene); U.S. Pat. No. 4,709,115 (simultaneous disproportionation of butene with itself to produce ethylene or propylene and hexene or pentenes and fractional distillation); and U.S. Pat. No. 6,583,329 (concurrent metathesis reaction and separation by fractional distillation to produce: (A) propylene from butene; (B) detergent range olefins from the metathesis of $C_{15}$ and heavier olefins with $C_9$ and lighter olefins; (C) 2-methyl-2-butene and propylene from the metathesis of 2-butene and isobutylene; and (D) tetramethylethylene from the metathesis of diisobutylene with itself and/or the reaction of diisobutylene with ethylene to produce neo hexene).

The metathesis of ethylene with n-butene to produce propylene is disclosed in U.S. Pat. No. 5,026,936. However, the purification of 2-butene prior to the metathesis reaction can be quite difficult. If pure 2-butene is not used, a wide range of byproducts are formed and/or the life the metathesis catalyst is shortened. The metathesis requires that the feed olefins be pretreated to remove contaminants such as dienes, water, sulfur, etc. These contaminants dramatically shorten the life of the catalyst. It is an advantage of the present invention that provides an integrated process for the recovery of high purity 2-butene and the conversion by metathesis with ethylene to propylene. It is a further advantage that an optional step in the integrated process provides purification of sulfur compounds and polyolefins from the 2-butene.

SUMMARY OF THE INVENTION

The principal elements of the present integrated process for the metathesis of 2-butene and ethylene to produce propylene are feeding a $C_4$ stream containing isobutene, isobutane, 1-butene and 2-butene to (1) a process for the isomerization of 1-butene to 2-butene and separation of the 2-butene in the presence of a particulate supported PdO catalyst prepared as a distillation packing, preferably in the presence of an effectuating amount of hydrogen, and the concurrent distillation of the isomerization product to recover 2-butene as bottoms and feeding the recovered 2-butene to (2) a process for the metathesis of 2-butene with ethylene in the presence of a metathesis catalyst whereby propylene is formed.

One embodiment of the present invention relates to essentially a three-step process wherein a mixed hydrocarbon feed, such as a light fluid cracked naphtha, containing butenes, butadiene and $C_5$'s, is first fed to a $C_4/C_5$ splitter (debutanizer) which removes the dienes and mercaptans by first reacting the mercaptans and dienes to form higher boiling sulfides. The remaining dienes are saturated to mono olefins. In the second step the $C_4$ stream is fed to a 2-butene enrichment column wherein the 1-butene is converted to 2-butene and the 2-butene separated from any isobutene by fractionation. In the final step the 2-butene is fed to a metathesis reactor along with ethylene wherein propylene is formed via the metathesis reaction.

Preferably all of the reactions are carried out in a distillation column reactor, that is, reaction and fractional distillation of the reactants and products are carried out concurrently in the distillation column reactor wherein the catalyst may be in the form to act as a distillation structure or part of a distillation structure or alternatively loose catalyst may be located in beds or zones preferably located within the distillation column reactor.

BRIEF DESCRIPTION OF THE DRAWING

The FIGURE is schematic flow diagram of an embodiment that illustrates the use of catalytic distillation for all of the steps in the invention.

DETAILED DESCRIPTION OF THE INVENTION

The process for the production of propylene by the metathesis reaction of ethylene with 2-butene preferably comprises the steps of:

(a) feeding hydrogen and a mixed $C_4$ stream containing 1-butene, 2-butene and isobutene to a first distillation column reactor containing a bed of hydroisomerization catalyst;

(b) concurrently in the first distillation column reactor,
  (i) isomerizing a portion of the 1-butene to 2-butene and
  (ii) separating the 2-butene in a 2-butene enriched stream from the isobutene by fractional distillation;

(c) removing the 2-butene enriched stream from the first distillation column reactor as a first bottoms;

(d) removing the isobutene from the first distillation column reactor as a first overheads;

(e) feeding said first bottoms and ethylene to a second distillation column reactor containing a bed of metathesis catalyst;

(f) concurrently in said second distillation column reactor,
  (i) reacting a portion the 2-butene and a portion of the ethylene in the presence of the metathesis catalyst to produce propylene, and
  (ii) separating unreacted ethylene and propylene from unreacted 2-butene and heavier material by fractional distillation;

(g) removing the unreacted ethylene and propylene from the second distillation column reactor as overheads; and (h) removing the unreacted 2-butene and heavier material from the second distillation column reactor as a second bottoms.

The reactions are preferably carried out under conditions of catalytic distillation. In a catalytic distillation, i.e., the catalyst serves as a distillation component The catalytic material is preferably a component of a distillation system functioning as both a catalyst and distillation packing, i.e., a packing for a distillation column having both a distillation function and a catalytic function: for example, rings, saddles, balls, irregular, sheets, tubes, spirals, packed in bags (as described in U.S. Pat. No. 4,242,530), plated on grills or screens, reticulated polymer foams (the cellular structure of the foams must be sufficiently large so as not to cause high pressure drops through the column or otherwise arranged, such as in chunks or concentration tubes to allow vapor flow) or honeycomb monoliths. The reaction system can be described as heterogenous since the catalyst remains a distinct entity.

The catalytic distillation process employs a catalyst system (See U.S. Pat. Nos. 5,730,843; 4,302,356; and 4,215,011) which provides for both reaction and distillation concurrently in the same reactor, at least in part within the catalyst system. The method involved is briefly described as one where concurrent reaction and distillation occur in combination reaction-distillation structures which are described in several U.S. Patents, namely U.S. Pat. Nos. 4,242,530; 4,250,052; 4,232,177; 4,302,356; 4,307,254; and 4,336,407. Additionally U.S. Pat. Nos. 4,302,356 and 4,443,559 disclose catalyst structures which are useful as distillation structures.

In addition to the catalytic systems described above, reactive distillation systems such as those disclosed in U.S. Pat. Nos. 4,536,373, 4,774,364, 4,847,430 and 5,510,089, which are incorporated herein, may be used to carry out the present process.

The particulate catalyst material may be a powder, small irregular chunks or fragments, small beads and the like. The particular form of the catalytic material in the cloth pockets is not critical, so long as sufficient surface area is provided to allow a reasonable reaction rate. The sizing of catalyst particles can be best determined for each catalytic material (since the porosity or available internal surface area will vary for different material and of course affect the activity of the catalytic material).

The distillation column reactor can be appreciated to contain a vapor phase and some liquid phase as in any distillation. The success of the concurrent distillation and reaction approach lies in an understanding of the principles associated with distillation. First, because the reaction is occurring concurrently with distillation, the initial reaction products are removed from the reaction zone as quickly as possible. Second, because all the components are boiling the temperature of reaction is controlled by the boiling point of the mixture at the system pressure. The heat of reaction simply creates more boil up, but no increase in temperature. Third, the reaction has an increased driving force because the reaction products have been removed and cannot contribute to a reverse reaction (LeChatelier's Principle).

As a result, a great deal of control over the rate of reaction and distribution of products can be achieved by regulating the system pressure. Also, adjusting the throughput (residence time=liquid hourly space velocity$^{-1}$) gives further control of product distribution and degree of conversion to metathesis product.

The temperature in a distillation column reactor is determined by the boiling point of the liquid mixture present at any given pressure. The temperature in the lower portions of the column will reflect the constitution of the material in that part of the column, which will be higher than the overheads; that is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa.

A reflux is preferably included in the system. The reflux ratio could vary over the rate 0.25:1 to 33:1. In practice, the higher ratio may be used to compensate for a short catalyst bed such as required for experimental work. In commercial size units the catalyst bed would be provided so that lower reflux and hence higher unit productivity could be obtained at lower operating cost.

Removal of Contaminants

The preferred process for the removal of mercaptans and polyolefins (such as dienes) is by selective hydrogenation combined with thioetherification. The light cracked naphtha stream which is used as the feed contains $C_4$ to $C_8$ components which may be saturated (alkanes), unsaturated (olefins) and polyunsaturated (diolefins) along with minor amounts of the mercaptans. The light naphtha is fed to a debutanizer which is a fractional distillation column to remove that portion containing the $C_5$ and higher boiling materials ($C_5+$) as bottoms and the $C_4$ and lower boiling materials ($C_4-$) as overheads. One embodiment of the present invention utilizes the upper portion of the debutanizer to react substantially all of the mercaptans and/or hydrogen sulfide ($H_2S$) contained in the light cracked naphtha with a portion of the diolefins to form sulfides which are higher boiling than the $C_5$ fraction containing the amylenes which are fed to the etherification and/or alkylation unit. The sulfides are removed as bottoms from the debutanizer column along with $C_5+$ bottoms.

The catalysts useful for the reaction include a reduced nickel, Pd or mixture preferably 5 to 80 wt. % nickel, such as nickel on an alumina base which has been configured as a catalytic distillation structure.

Hydrogen is provided as necessary to support the reaction. The distillation column reactor is operated at a pressure such that the reaction mixture is boiling in the bed of catalyst. A "froth level" may be maintained throughout the catalyst bed by control of the bottoms and/or overheads withdrawal rate which may improve the effectiveness of the catalyst thereby decreasing the height of catalyst needed.

The process preferably operates at overhead pressure of said distillation column reactor in the range between 0 and 250 psig and temperatures within said distillation reaction zone in the range of 100 to 300° F., preferably 130 to 270° F.

The feed and the hydrogen are preferably fed to the distillation column reactor separately or they may be mixed prior to feeding. A mixed feed is fed below the catalyst bed or at the lower end of the bed. Hydrogen alone is fed below the catalyst bed and the hydrocarbon stream is fed below the bed to about the mid one-third of the bed. The pressure selected is that which maintains catalyst bed temperature between 100° F. and 300° F.

Concentration of 2-butene

The process for concentrating 2-butene concurrently isomerizes 1-butene to 2-butene and separates the isobutene as overheads by fractional distillation in the presence of a particulate supported Pd, Rh, Ru, Ni or mixed catalyst prepared as a distillation packing, preferably in the presence of an effectuating amount of hydrogen. In addition any unconverted butadiene is saturated to butenes. The 2-butene has a boiling point significantly different from isobutene to allow for separation. Most (>95%) of the 1-butene is isomerized to 2-butene which is withdrawn as bottoms. This is accomplished by retaining the 1-butene within the catalyst bed while removing the 2-butene.

The feedstream which may derive from a thioetherification reactor, containing the mixed $C_4$'s is fed to the distillation column reactor containing a supported palladium oxide hydroisomerization catalyst along with sufficient hydrogen to provide for the hydrogenation of the butadiene and keep the hydroisomerization catalyst in the hydride state. In the distillation column reactor the butadiene is converted to butenes and 1-butene is isomerized to 2-butene which is concentrated in the bottoms. Isobutene and isobutane are withdrawn from the distillation column reactor as overheads.

Since the 2-butene is removed from the reaction zone as bottoms, the isomerization is driven away from equilibrium and more 2-butene is produced than is obtained in an equilibrium reactor (fixed bed flow through). Isobutane is also concentrated by distillation in the overheads along with the isobutene.

Any dissolved water will be removed from the distillation column reactor with the isobutene as overheads. The resultant 2-butene will thus be dry.

Metathesis

Suitable catalysts for the metathesis are the supported oxides of cobalt, molybdenum, rhenium or mixtures of cobalt and molybdenum oxides. Either silica or alumina-based supports for the oxides may be used. The distillation column reactor is generally operated at an overhead pressure to result in a catalyst bed temperature of 100-200° C. for $CoOMoO_3$ catalyst and about room temperature for the $Re_2O_7$ catalyst bearing in mind the effect of pressure on temperature as discussed above.

The reaction of 2-butene with ethylene to produce propylene is of interest because of the availability of the 2-butene and the value of propylene. The reaction is reversible in fixed bed reactors for a given residence time and may be written as follows:

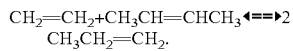
$$CH_2=CH_2+CH_3CH=CHCH_3 \rightleftharpoons 2\ CH_3CH=CH_2.$$

In a distillation column reactor, the equilibrium is constantly disturbed, thus although the equilibrium concentration of propylene at a given temperature is low, the removal of the propylene as an overhead product constantly drives the reaction to increase production of propylene. Adjusting the throughput gives further control of product distribution and degree of conversion to propylene. The production of undesirable side products, i.e., the isomerization of 2-butene to 1-butene, followed by their metathesis to pentenes and hexenes, is prevented or minimized.

Another advantage of the catalytic distillation reactor is that the feeds will be dried by azeotropic distillation allowing long periods of catalytic activity without the special drying steps that would otherwise be necessary. The necessity for dry feed is indicated in U.S. Pat. No. 3,340,322 where the dried feed is specified for the examples.

Referring now to the FIGURE a simplified flow diagram of one embodiment of the process may be seen in which del sulfur and polyolefins are removed in an optional first step. A typical light fluid cracked naphtha feed is fed via flow line 101 and combined with a recycle stream and fed to a first distillation column reactor 10 below a bed 12 of thioetherification catalyst where almost all of the mercaptans contained therein are reacted with dienes to form higher boiling sulfides. Hydrogen is fed as required below the bed 12 via flow line 118. In addition unreacted dienes are selectively hydrogenated to mono olefins. Concurrently with the reactions the light fluid cracked naphtha is split into a $C_4$ and lighter fraction which is taken as overheads via flow line 103 and a $C_5$ and heavier fraction, which contains the sulfides, which is removed as bottoms via flow line 104. The catalyst bed 12 is preferably in the rectification section of the distillation column reactor 10 because that is where the $C_4$'s will be concentrated. Standard distillation structures, such as sieve trays, bubble cap trays or packing is placed below the bed of catalyst as a stripping section where the hydrogen helps to strip the $C_4$'s back up the column into the bed 12.

The $C_4$ and lighter fraction is then fed to a second distillation column reactor which contains a bed 22 of isomerization catalyst where 1-butene is isomerized to 2-butene simultaneously with the removal of the isobutene and isobutane overheads via flow line 105. Hydrogen is fed below the bed 22 via flow line 119 to keep the catalyst in the hydride state and provide for any hydrogenation of dienes. Any water in the feed will also be taken along with the overheads. The water, isobutane and isobutene are condensed in condenser 24 and collected in receiver/separator 26 where the water is removed as a separate phase (not shown). The $C_3$'s and lighter are vented via flow line 110. Isobutane and isobutene are removed from the receiver/separator 24 via flow line 107 with a portion being returned to the second distillation column reactor 20 as reflux via flow line 109 and the remainder being removed as product via flow line 108. Catalyst bed 22 is placed in the rectification section where the 1-butene is concentrated for conversion to 2-butene. Standard distillation structures, such as sieve trays, bubble cap trays or packing is placed below the bed of catalyst as a stripping section where the hydrogen helps to strip the 1-butene back up the column into bed 22

The enriched 2-butene stream is removed from the second distillation column reactor 20 via flow line 106 and fed via flow to a third distillation column reactor 30 above a bed 32 of metathesis catalyst. Ethylene is fed to the third distillation column 30 below the bed 32 of metathesis catalyst via flow line 117. The ethylene reacts with the 2-butene in the catalyst bed 32 to produce propylene via the metathesis reaction and the product propylene is immediately removed as overheads via flow line 111 along with unreacted ethylene. Any unreacted 2-butene and heavier material is removed as bottoms via flow line 112 and recycled to the first distillation column reactor 10 where the heavies can be removed with the bottoms therefrom in flow line 104. The overheads in flow line 113 are fed to $C_2/C_3$ splitter 40 where the product propylene is separated from the unreacted ethylene and removed as bottoms via flow line 114. The unreacted ethylene is removed from the splitter 40 as overheads via flow line 112 and may be recycled (not shown). A portion of the propylene product may be returned to the third distillation column reactor as reflux via flow line 115 while the product propylene is removed via flow line 116.

The embodiment shown is for light fluid cracked naphtha. If a higher diene content stream is used, such as from a steam cracker, the diene content would be extremely high. Although it would still be possible to treat the dienes in the first distillation column reactor described above, it might be preferable to treat the stream in a separate reactor. In such a configuration a standard single pass down flow fixed bed thioetherification reactor could be placed before the naphtha splitter and a standard downflow fixed bed diene saturation reactor with recycle to control the heat of reaction located down stream.

The invention claimed is:

1. A process for the production of propylene by the metathesis reaction of ethylene with 2-butene comprising the steps of:
(a) feeding hydrogen and a light fluid cracked naphtha containing 1-butene, 2-butene, isobutene, mercaptans, dienes and $C_5$ and heavier components to a first distillation column reactor containing a thioetherification catalyst;
(b) concurrently in said first distillation column reactor,
  (i) reacting the dienes with the mercaptans in the presence of the thioetherification catalyst comprising nickel on an alumina base which has been configured as a catalytic distillation structure positioned in a rectification section of said first distillation column reactor at a pressure between 0 and 250 psig to maintain a temperature between 100 and 300° F. to form sulfides,
  (ii) reacting dienes with hydrogen to form mono olefins, and
  (iii) separating the light fluid cracked naphtha into a $C_4$ and lighter fraction and a $C_5$ and heavier fraction;
(c) removing the $C_4$ and lighter fraction containing the 1-butene, 2-butene and isobutene from the first distillation column reactor as a first overheads;
(d) removing the $C_5$ and heavier fraction containing the sulfides from the first distillation column reactor as a first bottoms;
(e) feeding said first overheads containing 1-butene, 2-butene and isobutene to a second distillation column reactor containing a bed of a supported palladium oxide hydroisomerization catalyst positioned in a rectification section of said distillation column reactor;
(f) concurrently in the second distillation column reactor,
  (i) isomerizing a portion of the 1-butene to 2-butene and
  (ii) separating the 2-butene in a 2-butene enriched stream from the isobutene by fractional distillation;
(g) removing the 2-butene enriched stream from the second distillation column reactor as a second bottoms;
(h) feeding said second bottoms and ethylene to a third distillation column reactor containing a bed of metathesis catalyst comprising supported oxides of cobalt or mixtures of cobalt and molybdenum;
(i) concurrently in the third distillation column reactor,
  (i) reacting a portion the 2-butene and a portion of the ethylene in the presence of the metathesis catalyst to produce propylene, and
  (ii) separating unreacted ethylene and propylene from unreacted 2-butene and heavier material by fractional distillation;
(j) removing the unreacted ethylene and propylene from the third distillation column reactor as a third overheads;
(k) removing the unreacted 2-butene and heavier material from the third distillation column reactor as a third bottoms;
(l) feeding the third overheads to a $C_2/C_3$ splitter where unreacted ethylene is removed as a third fourth overheads and propylene is removed as a fourth bottoms; and
(m) recycling the third bottoms containing unreacted 2-butene and heavies to said first distillation column reactor.

* * * * *